(12) United States Patent
Botzem et al.

(10) Patent No.: US 11,925,711 B2
(45) Date of Patent: Mar. 12, 2024

(54) METHOD OF MARKING FILM-LIKE DOSAGE FORMS

(71) Applicant: LTS Lohmann Therapie-Systeme AG, Andernach (DE)

(72) Inventors: Petra Botzem, Andernach (DE); Torsten Grunenberg, Nickenich (DE); Thomas Hille, Neuwied (DE); Peter Steinborn, Neuwied (DE)

(73) Assignee: LTS Lohmann Therapie-Systems AG, Andernach (DE)

( * ) Notice: Subject to any disclaimer, the term of this patent is extended or adjusted under 35 U.S.C. 154(b) by 125 days.

(21) Appl. No.: 15/771,307

(22) PCT Filed: Oct. 28, 2016

(86) PCT No.: PCT/EP2016/076143
§ 371 (c)(1),
(2) Date: Apr. 26, 2018

(87) PCT Pub. No.: WO2017/072328
PCT Pub. Date: May 4, 2017

(65) Prior Publication Data
US 2018/0311179 A1 Nov. 1, 2018

(30) Foreign Application Priority Data
Oct. 28, 2015 (EP) ..................................... 15191941

(51) Int. Cl.
| | | |
|---|---|---|
| *A61K 9/70* | (2006.01) | |
| *A61K 9/00* | (2006.01) | |
| *A61K 31/465* | (2006.01) | |
| *A61K 36/534* | (2006.01) | |
| *A61K 47/32* | (2006.01) | |
| *B29C 59/00* | (2006.01) | |
| *B29C 59/02* | (2006.01) | |
| *B29C 65/00* | (2006.01) | |
| *B29C 65/02* | (2006.01) | |
| *B65B 11/50* | (2006.01) | |
| *B65B 51/10* | (2006.01) | |
| *B29K 33/00* | (2006.01) | |
| *B29L 31/00* | (2006.01) | |

(52) U.S. Cl.
CPC ............ *A61K 9/7007* (2013.01); *A61K 9/006* (2013.01); *A61K 31/465* (2013.01); *A61K 36/534* (2013.01); *A61K 47/32* (2013.01); *B29C 59/005* (2013.01); *B29C 59/026* (2013.01); *B29C 65/02* (2013.01); *B29C 66/433* (2013.01); *B29C 66/849* (2013.01); *B65B 11/50* (2013.01); *B65B 51/10* (2013.01); *B29K 2033/12* (2013.01); *B29L 2031/712* (2013.01); *B29L 2031/753* (2013.01)

(58) Field of Classification Search
CPC .... A61K 31/465; A61K 36/534; A61K 47/32; A61K 9/006; A61K 9/7007; B29C 59/005; B29C 59/026; B29C 65/02; B29C 66/433; B29C 66/849; B65B 11/50; B65B 51/10; B29K 2033/12; B29L 2031/712; B29L 2031/753
USPC ....................................................... 424/747
See application file for complete search history.

(56) References Cited

U.S. PATENT DOCUMENTS

| | | | | |
|---|---|---|---|---|
| 4,828,108 A | * | 5/1989 | Roth | A61C 19/06 206/478 |
| 5,505,306 A | | 4/1996 | Akemi et al. | |
| 6,106,930 A | * | 8/2000 | Ludwig | A61J 3/007 428/156 |
| 7,396,321 B1 | * | 7/2008 | Flanagan | B65B 9/02 493/193 |
| 2006/0147493 A1 | * | 7/2006 | Yang | A61K 9/7007 424/439 |
| 2008/0242736 A1 | * | 10/2008 | Fuisz | A61K 9/0056 514/770 |
| 2009/0308964 A1 | * | 12/2009 | Chudy | B65B 61/28 242/597.1 |
| 2011/0200715 A1 | * | 8/2011 | Fuisz | A23F 5/36 426/103 |
| 2012/0076921 A1 | * | 3/2012 | Myers | A61K 31/47 427/2.14 |
| 2015/0360837 A1 | * | 12/2015 | Perez-Prat Vinuesa | C11D 17/042 206/524.7 |

FOREIGN PATENT DOCUMENTS

| | | |
|---|---|---|
| DE | 196 46 836 | 5/1998 |
| DE | 694 22 094 | 4/2000 |

(Continued)

OTHER PUBLICATIONS

Bala et al., Orally dissolving strips: A new approach to oral drug delivery system, Int J Pharm Investig. Apr.-Jun. 2013; 3(2): 67-76.*

(Continued)

*Primary Examiner* — Alma Pipic
(74) *Attorney, Agent, or Firm* — Lippes Mathias LLP

(57) ABSTRACT

Disclosed is a method for marking film-type dosage forms, comprising at least the positioning of a film-type dosage form between two layers of a sealable packaging material, the sectional heat-sealing of the two layers of the sealable packaging material so as to obtain an edge-sealed bag containing the film-type dosage form, and the blind-embossing of the film-type dosage form contained in the edge-sealed bag through at least one of the two layers of packaging material of the edge-sealed bag.

17 Claims, No Drawings

(56) References Cited

FOREIGN PATENT DOCUMENTS

EP         2641582 A1 * 9/2013 .............. A61J 3/078
WO   WO-2012007097 A2 * 1/2012 .............. B41F 13/40

OTHER PUBLICATIONS

International Preliminary Report on Patentability for corresponding Application No. PCT/EP2016/076143, 6 pages.
International Search Report for corresponding Application No. PCT/EP2016/076143, 5 pages including English Translation.
International Written Opinion of the International Search Authority for corresponding Application No. PCT/EP2016/076143 5 pages.

* cited by examiner

METHOD OF MARKING FILM-LIKE DOSAGE FORMS

The present application is a National Stage Entry of PCT/EP2016/076143, filed on Oct. 28, 2016, which claims priority to EP 15191941.2, filed on Oct. 28, 2015, the entirety of both is incorporated herein by reference.

The invention relates to film-like dosage forms. The invention relates in particular to a method of marking film-like dosage forms and to film-like dosage forms marked with this method.

The manufacturers of pharmaceutical products are ever more frequently obliged to provide not only the primary packaging of a pharmaceutical product with a marking identifying the product but also the dosage form itself. Marking of solid dosage forms, such as capsules, tablets or wafers, is commonly effected by printing them with the marking.

The printing of solid dosage forms to be administered orally or perorally is, however, controversial and/or problematic. Thus there is, for instance, discussion as to whether an increased allergy risk for the patient by the administration of the printed dosage form is connected with the application of the printing ink to the dosage form. In the case of film-like dosage forms, which contain a high proportion of oily constituents, such as plasticisers or essential oils, the use of aqueous printing inks is furthermore not possible for the printing because these printing inks do not adhere to the film-like dosage forms.

As an alternative to the printing of film-like dosage forms, it is proposed in European Patent EP0949908B1 that film-like dosage forms be provided with a watermark so that when one looks through them the film-like dosage forms have visible surface regions of different thickness. However, in order to manufacture film-like dosage forms with a watermark special carriers are necessary, for instance structured substrates or carriers with regions which are differently temperable.

An alternative possibility for marking film-like dosage forms consists of providing them with an embossing. However, it has transpired that embossing film-like dosage forms before they have been individually packaged does not result in a permanent marking of the dosage form. The embossing of the film-like dosage form disappears due to the sealing process which is necessary for packaging it individually because the temperature of about 150° C. to about 200° C. which is necessary for the sealing of individual film-like dosage forms in edge-sealed bags causes the film-like dosage form itself to soften so that a previously effected embossing disappears.

It was thus the object of the present invention to find a way of providing film-like dosage forms with a marking which is present even after sealing them in an edge-sealed bag and is permanently retained unchanged.

This object is solved by a method in which a film-like dosage form, which has already been sealed, is subjected to blind embossing, wherein the blind embossing of the film-like dosage form is effected by the use of high pressure and the avoidance of heat and through the packaging material.

Surprisingly, it has been found that embossing the film-like dosage form through the packaging material results in a permanent embossing and thus marking of the dosage form. It is assumed that the deformation of the packaging material accompanying the embossing process stabilises the embossing of the film-like dosage form so strongly that it remains permanently preserved.

In the context of the present disclosure, a film-like dosage form is understood to be a thin film-, foil- or wafer-shaped dosage form, which contains at least one active substance and commonly has an area of about 2 cm$^2$ to about 8 cm$^2$ and a thickness in the range of about 20 µm to about 500 µm. The term "film-like dosage form" includes not only single layer dosage forms but also laminates, in which the dosage form includes two, three or more layers. The film-like dosage form in the context of the present invention can be mucoadhesive. In the context of the present disclosure "film-like dosage form" further includes not only dosage forms which rapidly release the active substance but also dosage forms which slowly melt or dissolve after administration and also dosage forms which retain the active substance for a long time and release it approximately uniformly. The film-like dosage forms include at least one active substance-containing layer, in which at least one pharmaceutical active substance is contained in a polymer or polymer mixture. In the case of multi-layer film-like dosage forms, in addition to the at least one active substance-containing layer the dosage form can include at least one mucoadhesive layer and/or a rear layer, whereby the rear layer can be impermeable to the active substance.

The embossing of the film-like dosage form is effected in the method on the packaged product, that is to say on the packaged dosage form. The embossing is effected through the packaging material.

The method includes at least the following steps:
placing a film-type dosage form between two layers of sealable packaging material;
sectionally heat sealing the two layers of the sealable packaging material to form an edge-sealed bag containing the film-type dosage form;
blind embossing the film-type dosage form contained in the edge-sealed bag through at least one of the two packaging material layers of the edge-sealed bag.

The film-type dosage form is produced by methods known to the expert in the field of the production of film-type dosage forms. These methods include
the mixing of the components contained in the layer or in the individual layers of the dosage form, such as a polymer or polymer mixture, active substance and optionally at least one pharmaceutically acceptable excipient, into a solvent;
the spreading out or scraping of the solvent-containing composition onto a substrate;
the drying of the spread out composition in order to remove the solvent and to produce a polymer film;
the division of the polymer film into strips; and
the separation of individual dosage forms from the strips by cutting or stamping.

In the method a film-type dosage form is positioned between two layers of sealable packaging material. In one embodiment, the two layers of sealable packaging material are provided in the form of strip-shaped rolled product. In this embodiment, the packaging material strips are unrolled from the roll and supplied to the stations in which the dosage form is placed on one of the packaging material strips, the second packaging material strip is guided over it and is sealed. This embodiment enables a particularly rapid and reliable mechanical packaging and marking of the film-type dosage forms.

The sealable packaging material is impermeable to the active substance contained in the film-type dosage form. In a preferred embodiment, the sealable packaging material is a laminate including a metallic foil, for instance an aluminium foil, which is coated on one of its two surfaces with a sealable plastic material.

In the method, a first layer of sealable packaging material is provided, preferably by the first layer being unrolled from the rolled product in the form of a strip of the sealable packaging material.

The film-type dosage form is positioned on the surface of the sealable packaging material which is coated with the sealable plastic material and covered with the second layer of sealable packaging material such that its surface coated with a sealable plastic material is directed towards the film-type dosage form. The second layer of sealable packaging material is preferably also unrolled from a roll and supplied in the form of a strip. The strips of packaging materials with their surfaces provided with a sealable plastic material directed towards one another and the film-type dosage form arranged between them are heat sealed in sections so that an edge-sealed bag is produced, which contains the film-type dosage form. "In sections" means that the two sealable packaging materials are sealed together in the sections in which no film-type dosage form is present, that is to say along the longitudinal edges of the strip-shaped packaging materials and in the regions between successive film-type dosage forms.

The heat sealing of the two sealable strips of packaging material is effected under pressure and with a temperature conventional for heat sealing of between 150° C. and 200° C.

In a further step of the method, the film-type dosage forms sealed in between the two layers of packaging material are provided with a marking by blind embossing. The embossing of the packaged dosage form must be effected with a pressure which is high enough to emboss the dosage form through the layer of packaging material. The pressure must, however, not be so high that the packaging material is destroyed in the embossing process.

In an additional and/or alternative embodiment, the embossing of the packaged dosage form is effected with a pressure of not more than 10 bar, preferably not more than 9 bar, particularly preferably not more than 8 bar and most particularly preferably not more than 7 bar.

The embossing of the film-type dosage form is effected with the avoidance of heat. This means also that the embossing tools used for the embossing (matrix and/or patrix) are not heated. In one embodiment, the embossing tools used for the embossing are cooled in order to counteract heating of the embossing tools which occurs during the embossing process. The embossing tools are preferably cooled to room temperature, that is to say to a temperature of between about 18° C. to about 23° C. In an alternative embodiment, the embossing tools are cooled to a temperature of about 4° C.

The marking of the film-type dosage form sealed in between the two layers of packaging material is a blind embossing, that is to say embossing of the marking without ink.

In one embodiment, the blind embossing is flat embossing. In flat embossing, deformation (compressions) of the material occurs in the region of the force application position under the action of pressure by the use of an embossing tool (embossing stamp, embossing roller, embossing wheels) as a high pressure mould. Due to the pressure effect, which is used in a targeted manner, of the embossing tool, a profile-like reshaping of the material occurs on the embossed side, whereby the rear surface of the film-type dosage form, which is sealed in between two layers of sealable packaging material, remains flat. The rear layer of the two layers of sealable packaging material engages a flat support or counterroller during the embossing process.

In an additional or alternative embodiment, the flat support or the counterroller has an elastic surface with a high restoring force, which is engaged by the rear layer of the two layers of sealable packaging material. In this embodiment, a profile-like reshaping of the material occurs on the rear surface of the film-like dosage form sealed in between two layers of sealable packaging material. This embodiment results in a marking of the film-type dosage form which is more readily perceptible.

In a further and/or alternative embodiment, the embossing is effected in the form of relief embossing. With relief embossing, a plastic deformation of the embossed material occurs. In this, the material to be embossed is compressed between an embossing die (matrix) and a counterform (patrix) with the use of pressure. Not only does compression of the material occur but also stretching of the material structure at the edges of the motif. Relief embossing can be effected by means of an embossing stamp or an embossing roller. Relief embossing results in a particularly distinct haptic effect.

The embossed marking can be numbers, letters, graphic symbols, shapes and combinations thereof.

In one embodiment, the method further includes the separation of individual edge-sealed bags, which contain a film-type dosage form, comprising a strip of two layers of sealable packaging material sealed together in sections. The separation of the individual edge-sealed bags is effected by cutting the strip or by stamping out from the strip.

The separation of the edge-sealed bags, which contain a film-type dosage form, from the strip can be effected before or after the embossing of the sealed in film-type dosage form.

In one embodiment, the method includes the following steps:
a) placing a film-type dosage form between two layers of sealable packaging material;
b) sectionally heat sealing the two layers of the sealable packaging material to form an edge-sealed bag containing the film-type dosage form;
c) blind embossing the film-type dosage form contained in the edge-sealed bag through at least one of the two packaging material layers of the edge-sealed bag.
d) separating individual edge sealed bags, which contain a film-type dosage form.

In an alternative embodiment, the embossing of the packaged dosage forms occurs before the separation of the individual packages. In this embodiment the method includes the following steps:
a) placing a film-type dosage form between two layers of sealable packaging material;
b) sectionally heat-sealing the two layers of the sealable packaging material to form an edge-sealed bag containing the film-type dosage form;
c) separating individual edge-sealed bags which contain a film-type dosage form; and
d) blind embossing the film-type dosage form contained in the edge-sealed bag through at least one of the two packaging material layers of the edge-sealed bag.

In accordance with the second aspect, the invention relates to film-type dosage forms which have a marking in the form of an embossing. The film-type dosage is or was in an edge-sealed bag. The film-type dosage form is markable with the method described above and preferably the film-type dosage form is with the method described above.

In one exemplary embodiment, the film type dosage form is a heavy oily film. In the context of the present invention, a heavy oily film is to be understood as a film-type dosage form which contains a high proportion of plasticisers and/or essential oils. The term "high proportion" refers to a content of oily substances which is so high that the tendency for the bleeding of this substance or these substances out of the film at room temperature can not be prevented. The absolute content of oily substances from which bleeding occurs is dependant on, amongst other things, the polymer and the oily substance. What is crucial is how easily soluble the oily substance is in the polyerm.

EXEMPLARY EMBODIMENT

A film, which rapidly dissolves in the oral cavity, based on a copolymer of methacrylic acid and ethyl acetate (1:1) (Eudragit® L 100-55 from the company Evonik Nutrition Care GmbH) containing 2.5 mg nicotine and 6.64 mg mint oil was subjected to blind embossing in which an embossing stamp pressed a two digit number about 8 mm high with a pressure of 2 bar into the film. After sealing into two layers of aluminium foil laminated with sealable plastic material the marked films were stored at room temperature without being pressed. After a storage period of at most four weeks no embossing was visible on the unpacked films.

In parallel with the aforementioned control experiment, the same films were firstly sealed in the same packaging material and then subjected to blind embossing in which an embossing stamp pressed a two digit number about 8 mm high with a pressure of 2 bar into the film through one layer of packaging material. After storing for more than half a year, no change in the marking of the films in comparison with an identical marking directly after embossing could be detected.

The invention claimed is:

1. A method of marking film-type dosage forms comprising the following steps:
    placing a film-type dosage form between two layers of sealable packaging material;
    sectionally heat sealing the two layers of the sealable packaging material to form an edge-sealed bag containing the film-type dosage form; and
    relief embossing, using embossing tools, the film-type dosage form contained in the edge-sealed bag through at least one of the two packaging material layers of the edge-sealed bag;
    wherein the relief embossing of the film-like dosage form is effected by the use of high pressure and the avoidance of heat;
    wherein the sealable packaging material is a laminate including a metallic foil;
    wherein the two layers of sealable packaging material are provided in the form of a strip-shaped rolled product; and
    wherein the embossing tools are cooled to room temperature.

2. The method as claimed in claim 1, wherein the relief embossing is effected with a pressure of at least 2 bar and not more than 10 bar.

3. The method as claimed in claim 1, wherein the relief embossing, using embossing tools, is effected with at least one embossing tool selected from the group consisting of embossing stamps, embossing wheels, and embossing rollers.

4. The method as claimed in claim 1, wherein the relief embossing forms at least one mark on the film-type dosage form selected from the group consisting of numbers, letters, symbols, shapes, and combinations thereof.

5. The method as claimed in claim 1, further comprising:
    sectionally heat sealing the two layers of the sealable packaging material to form a second edge-sealed bag containing a second film-type dosage form; and
    separating the edge-sealed bag from the second edge-sealed bag.

6. The method as claimed in claim 5, wherein the edge-sealed bag is separated from the second edge-sealed bag before the relief embossing.

7. The method as claimed in claim 5, wherein the edge-sealed bag is separated from the second edge-sealed bag after the relief embossing.

8. The method as claimed in claim 3, wherein the embossing tool creates a profile-like reshaping of the material on the rear surface of the film-like dosage form.

9. The method as claimed in claim 1, wherein a first of the two layers of sealable packaging material is unrolled and the film-type dosage form placed thereon and a second of the two layers of sealable packaging material is unrolled and guided over the film-type dosage form and the first of the two layers of sealable packaging material.

10. The method of claim 9, wherein the laminate includes a surface coated with a sealable plastic material and wherein the sealable plastic material of the first of the two layers of sealable packaging material and the sealable plastic material of the second of the two layers of sealable packaging material face one another.

11. The method of claim 3, wherein a layer of the two layers of the sealable packaging material opposed to the layer through which embossing is performed engages a flat support or counter roller during the embossing process.

12. The method of claim 11, wherein the flat surface or the counter roller has an elastic surface.

13. The method of claim 1, wherein the sealable packaging material is impermeable to an active substance in the film-type dosage form.

14. The method of claim 13, wherein the film-type dosage form comprises a heavy oily film.

15. A film-like dosage form comprising an embossed marking formed according to the method as claimed in claim 1.

16. The film-like dosage form as claimed in claim 15, wherein the film-like dosage form is present in an edge-sealed bag.

17. The film-like dosage form as claimed claim 15, wherein the film-like dosage form is a heavy oily film.

* * * * *